(12) United States Patent
Matthiessen et al.

(10) Patent No.: US 7,941,210 B2
(45) Date of Patent: May 10, 2011

(54) ELECTROIMPEDANCE TOMOGRAPH WITH COMMON-MODE SIGNAL SUPPRESSION

(75) Inventors: Hans Matthiessen, Bad Schwartau (DE); Dieter Weismann, Gross Grönau (DE); Jianhua Li, Lübeck (DE); Yvo Gärber, Lübeck (DE); Arndt Pöcher, Bad Schwartau (DE); Markus Steeger, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 1350 days.

(21) Appl. No.: 11/427,516

(22) Filed: Jun. 29, 2006

(65) Prior Publication Data

US 2007/0010758 A1    Jan. 11, 2007

(30) Foreign Application Priority Data

Jul. 7, 2005   (DE) .................... 10 2005 031 752

(51) Int. Cl.
*A61B 5/05*       (2006.01)
*G01R 27/00*    (2006.01)
*G01R 27/08*    (2006.01)

(52) U.S. Cl. .................. 600/547; 324/600; 324/692
(58) Field of Classification Search .................. 600/547, 600/425, 442, 506, 529; 324/612, 613, 625, 324/627, 628
See application file for complete search history.

(56) References Cited

U.S. PATENT DOCUMENTS 5,640,314 A * 6/1997 Glasband et al. ............... 363/36
6,236,886 B1 5/2001 Cherepenin et al.
7,288,943 B2 * 10/2007 Matthiessen et al. ......... 324/628
2004/0158167 A1 * 8/2004 Smith et al. .................... 600/547
2005/0203431 A1 9/2005 Brodnick et al.

FOREIGN PATENT DOCUMENTS

DE     2 253 861        5/1974
DE     102005011769   9/2005
EP     0 855 875 B1   8/1998

OTHER PUBLICATIONS

J. Rosell, P. Riu, "Common-mode feedback in electrical impedance tomography", IN: Clinical physics and physiological measurement, 1992, vol. 13, Suppl A, S. 11-14.

* cited by examiner

*Primary Examiner* — Max Hindenburg
*Assistant Examiner* — Devin Henson
(74) *Attorney, Agent, or Firm* — McGlew and Tuttle, P.C.

(57) ABSTRACT

An electroimpedance tomograph with a plurality of electrodes (1) is provided, which can be placed on the body of a patient and are connected via a selector switch (60) with a control and evaluating unit (20). The control and evaluating unit (20) cooperates with the selector switch (60) such that two electrodes each are supplied with an alternating current from an AC power source (22) and the detected analog voltage signals of the other electrodes are processed in order to reconstruct therefrom the impedance distribution of the body in the plane of the electrodes, wherein a symmetrical AC power source is used to reduce common-mode signals. To further suppress interferences due to common-mode signals, provisions are made for the control and evaluating unit (20) to be set up, furthermore, for detuning the common-mode signal of the alternating current on the body against the ground by means of a common-mode signal measuring electrode (4) and, based on this, the symmetry of the symmetrical AC power source such that the common-mode signal on the body is minimized, and the corresponding detuning parameters are stored for each electrode pair.

21 Claims, 3 Drawing Sheets

ELECTROIMPEDANCE TOMOGRAPH WITH COMMON-MODE SIGNAL SUPPRESSION

CROSS REFERENCE TO RELATED APPLICATIONS

This application claims the benefit of priority under 35 U.S.C. §119 of German Patent Application DE 10 2005 031 752.9 filed Jul. 7, 2005, the entire contents of which are incorporated herein by reference.

FIELD OF THE INVENTION

The present invention pertains to an electroimpedance tomograph with a plurality of electrodes, which can be arranged on the body of a patient and which are connected via a selector switch to a control and evaluating unit, wherein the control and evaluating unit cooperates with the selector switch such that two electrodes each are supplied with alternating current rotatingly from an AC power source and the detected analog voltage signals of the other electrodes are sent into the control and evaluating unit via a measuring amplifier and are processed there in order to reconstruct from this the impedance distribution of the body in the plane of the electrodes, a symmetrical AC power source being used to reduce common-mode signals.

BACKGROUND OF THE INVENTION

A measuring technical problem in electroimpedance tomography is that the useful signal used to calculate the graphic representation must be sufficiently larger than the particular interferences. The simple increase in the measuring current has limits, because the currents that are permissible according to the standards are limited (in a frequency-dependent manner). Consequently, it is necessary to reduce the interference signals. Moreover, the interference signals consist partly of self-generated interferences, e.g., the crosstalk or the so-called common-mode signal, which increase proportionally to the increase in the current. Increasing the measuring current can improve the distance from the external interferences at best.

Electrical impedance tomography (EIT) is a method for reconstituting impedance distributions or, in case of functional EIT for reconstituting impedance changes relative to a reference distribution, in electrically conductive bodies. A plurality of electrodes are arranged for this purpose on the conductive surface of the body being examined, and the control unit, usually a digital signal processor, ensures that a pair of (preferably) adjacent electrodes each is supplied consecutively with an electric alternating current (for example, 5 mA at 50 kHz), and the electric voltages are detected at the remaining electrodes acting as measuring electrodes and are sent to the control unit. The impedance distribution or, in case of functional electroimpedance tomography, the change in that impedance distribution relative to a reference distribution can be reconstructed with suitable algorithms by the combination of the measured voltage values during the consecutive rotating current feeds. A ring-shaped, equidistant arrangement of 16 electrodes is used in typical cases, and these electrodes can be placed around the body of a patient, for example, with a belt. Alternating current is fed into two adjacent electrodes each, and the voltages are measured between the remaining currentless electrode pairs acting as measuring electrodes and recorded by the control unit. By rotating the current feed points, a plurality of measured voltage values are obtained, from which a two-dimensional tomogram of the impedance distribution can be reconstructed relative to a reference in the plane of the electrode.

Such tomograms are of interest in medicine because the impedances depend on the biological state of the organs (for example, the breathing state of the lungs) and/or the frequency of the current. Therefore, both measurements at different states are performed at a given feed frequency and in different biological states (for example, observation of the breathing cycles) and measurements at different frequencies performed at different feed frequencies and identical biological state in order to obtain information on the corresponding impedance changes. As was already mentioned, functional impedance tomography of the lungs, in which the electrodes of the EIT device are arranged around the patient's thorax, is an important application. One of the interferences occurring in terms of measuring technique during impedance tomography is the ultimately unavoidably occurring residual asymmetry of the alternating current feed on the body, which also occurs when a symmetrical AC power source is used, which is due to the differences in the routing of the cables to the different electrodes, different contact resistances, etc.

The power source supplies an alternating current alternating between 20 kHz and several MHZ for the measurement. To evaluate the causes of the development of the asymmetry of current feed, it is consequently necessary to use not only disturbing differences in the ohmic resistances but also those in the AC impedances. The use of alternating current is necessary for medical reasons. The permissible measuring currents would be even lower by several orders of magnitude in case of direct current. Moreover, the measurement with alternating current makes possible a low-drift, frequency-selective demodulation of the measuring currents and to obtain information on how the impedances of the upper body change with the frequency.

FIG. 3 shows a basic circuit diagram of an electroimpedance tomograph of the type mentioned in the introduction, which embodies a symmetrical AC power source due to the insertion of a power source 22 or an isolation transformer 40 between the AC power source 22 and the selector switch (multiplexer) 60. The primary circuit of this isolation transformer 40 has clear references and consequently usually asymmetries to the ground (the measuring technical reference point of the device) due to the circuitry. To keep the effect of the asymmetry on the secondary side as limited as possible via stray capacitances, a shield winding, which is grounded, is located between the two windings. If no asymmetrical stray capacitances of the secondary side are desired against this shield winding, the secondary winding must have a symmetrical design in relation to the shield winding. This symmetrical design has, of course, limits, so that the stray capacitances must be assumed to be different on both sides of the secondary winding in relation to the ground in an equivalent circuit. This is only one example of how extensive symmetry of the alternating current feed is sought to be achieved.

FIG. 4 shows an equivalent circuit to explain the asymmetries of the AC signal applied in the device from FIG. 3. Asymmetries in the power source are only part of the asymmetries occurring in the measuring circuit. Other causes are the multiplexer or selector switch 60, which has different conducting-state DC resistances $R_{ML}$ and $R_{MR}$ for the two terminals (depending on the channel being used) and also different stray capacitances $C_{ML}$ and $C_{MR}$ in relation to the electric environment. The multiplexer 60 is followed by the shielded connecting line, so that the capacitive differences in $C_{LR}$ and $C_{LL}$ against the ground of the two connecting lines to the electrodes are to be taken into account. The inductive and resistive line impedances $Z_{LL}$ and $Z_{LR}$ are other sources of asymmetry especially in case of differences in the lengths of the connecting lines and at high measuring current frequencies.

Finally, the transition impedances of the electrodes against the skin surface are finite and different, which is likewise to be taken into account. Moreover, they are complex, i.e., they are composed mainly of the transition resistances $R_{EL}$ and $R_{ER}$ and the transition capacitances $C_{EL}$ and $C_{ER}$.

All asymmetries combined cause that there are different flows of measuring currents from the two lines via the stray capacitances against the ground and different voltage drops at the longitudinal impedances and consequently there are differences in current flow between the two feed terminals, because more or less different current components will have now flown to the ground before and the differential current flows to the ground via the body resistance and the transition impedance of the reference ground electrode and thus it generates a common-mode signal on the body and consequently on the measuring electrodes. This common-mode signal is different for all actuated electrode positions both because of the differences in the channels of the multiplexer 60 as well as the external lines and of the electrode transition resistances and generates at the measuring amplifier error signals, which may overlap the useful signals, together with the value and the differences of the transition impedances of the particular measuring electrodes (which are connected by the multiplexer 60) with the finite common-mode reduction resulting therefrom.

Even if the measuring amplifier behind the multiplexer were ideal, the electrodes of the particular connected measuring lines would again generate asymmetries and only a finite common-mode signal suppression in a manner that is the reverse of what happens in case of the current path via the parasitic impedances and the values thereof, which differ from one measuring channel to the next.

One possibility of keeping this common-mode signal as low as possible is a reference ground electrode with a very low transition impedance. The size of the possible reference ground electrodes and their ability to be handled are limited and, beginning from a certain size, they generate movement artifacts, which originate from the changes in the transition impedance that are generated during the movement of the patient. Therefore, this measure only has limited effectiveness.

SUMMARY OF THE INVENTION

The object of the present invention is therefore to provide an electroimpedance tomograph in which interferences with the measured signals due to common-mode signals are further suppressed.

According to the invention, an electroimpedance tomograph is provided with a plurality of electrodes, which can be placed on the body of a patient and are connected via a selector switch with a control and evaluating unit. The control and evaluating unit cooperates with the selector switch such that two electrodes each are supplied with an alternating current from an AC power source and the detected analog voltage signals of the other electrodes are processed in order to reconstruct therefrom the impedance distribution of the body in the plane of the electrodes. A symmetrical AC power source is used to reduce common-mode signals. The control and evaluating unit is set up, furthermore, to detune the common-mode signal of the alternating current on the body against the ground by means of a common-mode signal measuring electrode and, based on this, the symmetry of the AC power source such that the common-mode signal on the body is minimized, and the corresponding detuning parameters are stored for each electrode pair.

According to another aspect of the invention, an ectroimpedance tomograph is with a plurality of electrodes, which can be placed on the body of a patient and are connected to a control and evaluating unit. The control and evaluating unit cooperates with the selector switch such that two electrodes each are supplied with an alternating current from an AC power source. The detected analog voltage signals of the other electrodes are processed in order to reconstruct therefrom the impedance distribution of the body in the plane of the electrodes. A symmetrical AC power source is used to reduce common-mode signals. An analog control loop circuit with a differential amplifier is present, where one input of the differential amplifier is connected to the ground and the other input thereof is connected to the output of a common-mode signal measuring electrode, which supplies the common-mode signal of the alternating current on the body. The output of the differential amplifier is connected to a center tap of the symmetrical AC power source in order to detune this power source such that the common-mode signal on the body is minimized.

Provisions are made according to the present invention according to the first alternative for the device to be set up to record the common-mode signal of the alternating current on the body against the ground with a common-mode signal measuring electrode. The measured common-mode signal is processed in the control and evaluating unit. The control and evaluating unit is set up for this purpose to detune the symmetry of the symmetrical power source on the basis of the measured common-mode signal, i.e., to shift the zero point of the power source, such that the common-mode signal on the body is compensated, i.e., minimized as extensively as possible. The parameters can thus be determined according to value and phase for each electrode pair for the detuning of the symmetrical AC power source and stored in the control and evaluating unit. The control and evaluating unit is then set up preferably such that the detuning parameters being stored for the particular electrode pair to be connected can be polled in the range of measurement and the symmetrical AC power source is detuned in the manner optimal for that electrode pair, so that the common-mode signal for the current electrode pair is minimized.

In a preferred embodiment, the control and evaluating unit is connected to a compensation AC power source, whose output is superimposed to the symmetrical AC power source. The control and evaluating unit controls the compensation AC power source according to the measured common-mode signal in terms of amplitude and phase such that the symmetry of the symmetrical AC power source is detuned such as to minimize the common-mode signal on the body.

In another preferred embodiment, passive compensation members are connected to a first output of the symmetrical AC power source, one compensating member being connected, in particular, via a resistor and a control transistor and one compensation member being connected via a capacitor and a control transistor, e.g., to the ground. The control and evaluating unit is set up to control the compensation members via their control transistors according to the measured common-mode signal such that the symmetry of the AC power source is detuned such as to minimize the common-mode signal on the body. The other output of the symmetrical AC power source is preferably detuned in advance in the opposite sense, so that an adjusting point can be obtained with certainty according to value and phase at the first output by the active reaction of the controllable compensation members in order to minimize the common-mode signal on the body.

Possible control algorithms for controlling the compensation power source or the detuning with passive compensation members are known. If linear control algorithms do not lead to fully satisfactory results, rule-based (fuzzy) algorithms are preferably used.

According to the second, alternative aspect of the present invention, provisions are made for an analog control loop circuit with a differential amplifier to be present, which amplifier receives as the input variables the ground and the output signal of a common-mode signal measuring electrode, which supplies the common-mode signal of the alternating current on the body. The output of the differential amplifier of the analog control loop circuit is fed into the center tap of the symmetrical AC power source in order to detune this such that the common-mode signal on the body is minimized. In this embodiment, the detuning of the AC power source is carried out by the analog control circuit simultaneously for each electrode pair in the measuring mode.

The present invention will be described below on the basis of exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
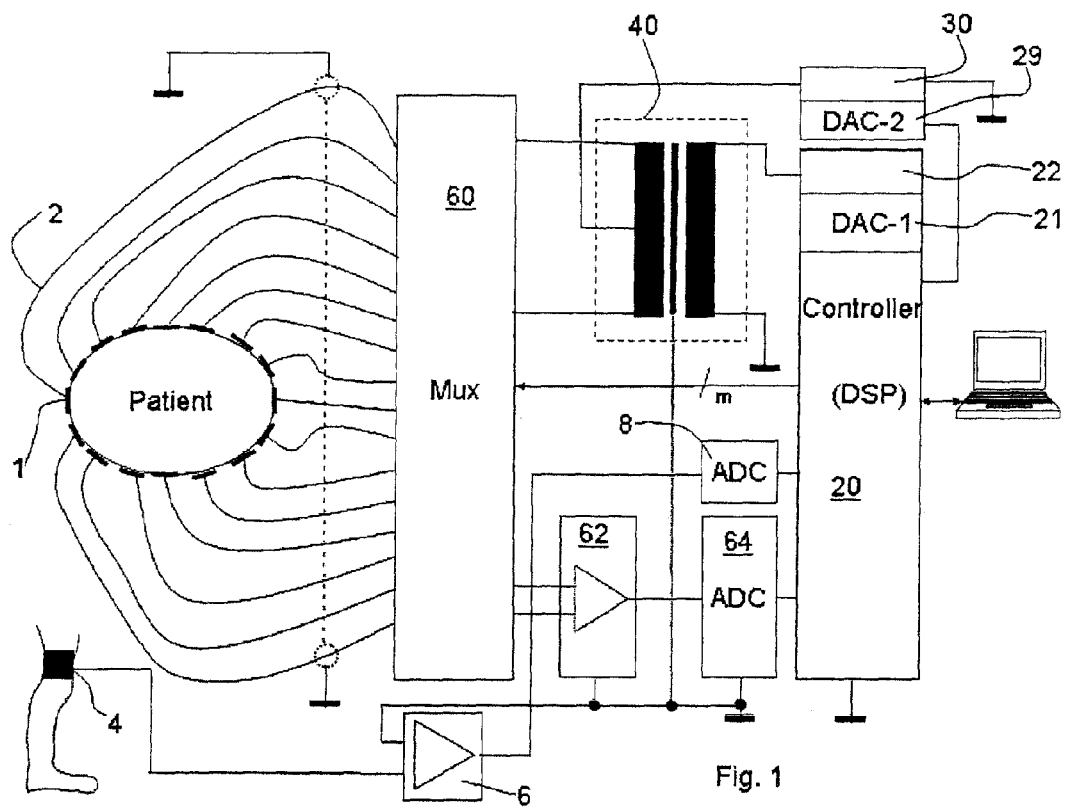
FIG. 1 is a block diagram of a first embodiment of an electroimpedance tomograph.

Referring to the drawings in particular, the electroimpedance tomograph shown in FIG. 1 has a control and evaluating unit 20, which is connected via a digital-analog converter 21 to an AC power source 22 for controlling same. The AC power source 22 with portions of the control and evaluating unit 20 form an overall AC power unit generating the applied alternating current which is actually applied to the patient. The alternating current of the power source 22 is galvanically separated from the selector switch 60 via an isolation transformer or transformer 40. The selector switch or multiplexer 60 applies the AC applied current signal with the cable 2 to two electrodes 1 each (only one of a total of 16 electrodes is provided with a reference number). The other electrodes are then used consecutively as measuring electrodes in pairs. The voltage signals of the measuring electrodes are sent to the control and evaluating unit 20 via the multiplexer 60 and a differential amplifier 62 and an analog-digital converter 64. The feeding electrode pairs 1 rotate now around the patient's body, controlled by the control and evaluating unit 20 and the multiplexer 60, and an electroimpedance tomogram is generated from this sequence in the control and evaluating unit 20.

Furthermore, a common-mode signal measuring electrode 4, which is to measure the common-mode signal of the body against ground, is provided.

The signal of the common-mode signal measuring electrode 4 is sent to the control and evaluating unit 20 via a measuring amplifier 6 and an analog-digital converter 8. The control and evaluating unit 20 is connected to a compensation AC power source 30 via a digital-analog converter 29. The control and evaluating unit 20 is set up to control the compensation AC power source 30 according to value and amplitude on the basis of the value of the common-mode signal on the body, which value is supplied via the analog-digital converter 8, such that the symmetry of the primary AC power source 22 is detuned on the secondary side of the isolation transformer 40 as a result such that the common-mode signal measured on the body with the common-mode signal measuring electrode 4 is minimized.

The compensation AC power source 30 may be connected, as is shown, to the center tap of the secondary winding of the isolation transformer 40. As an alternative, the alternating current of the compensation AC power source 30 may also be sent to one of the terminals of the secondary winding of the isolation transformer 40. The control of the compensation AC power source 30 by the control and evaluating unit 20 depends, of course, on where the compensation alternating current is fed.

Figure 2:
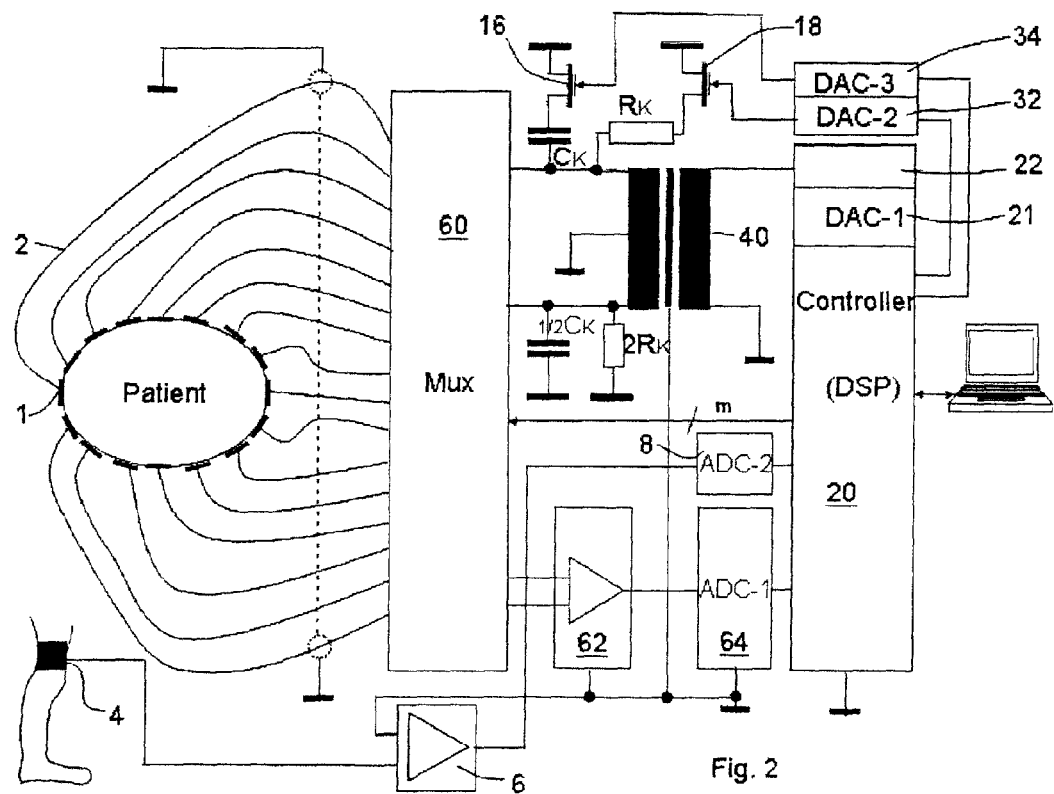
FIG. 2 is another embodiment of an electroimpedance tomograph.
Figure 3:
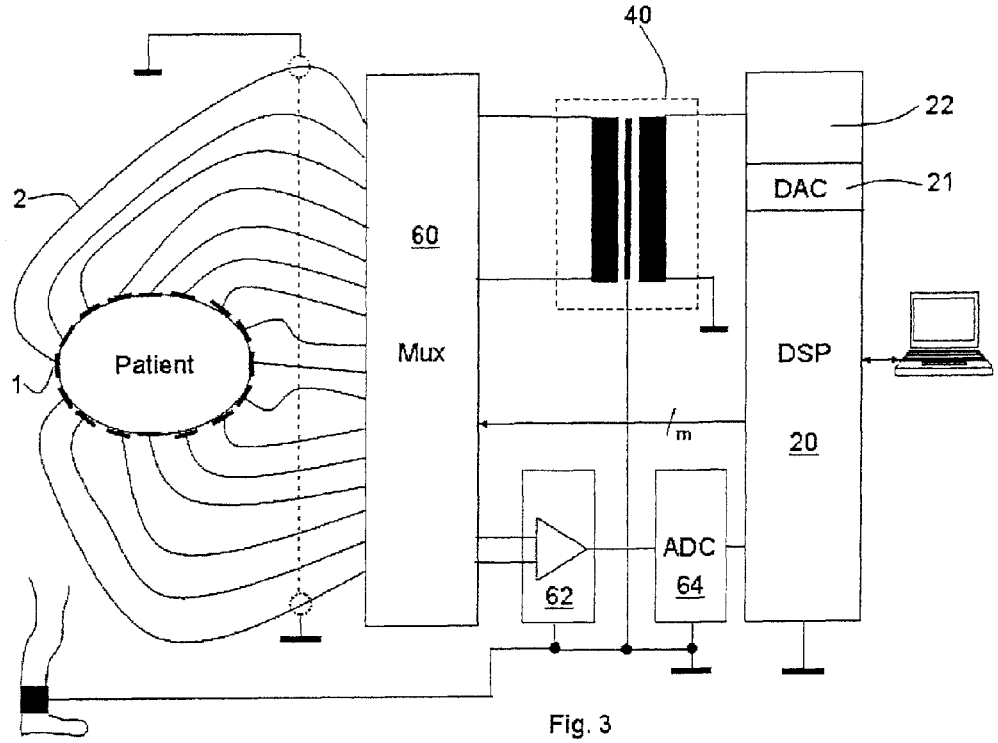
FIG. 3 is a block diagram of an electroimpedance tomograph according to the state of the art.

In the alternative embodiment according to FIG. 2, the common-mode signal on the body is fed again to the control and evaluating unit 20 via the common-mode signal measuring electrode 4, the measuring amplifier 6 and the analog-digital converter 8.

Unlike in the case of the active detuning of the primary AC power source 22 by a compensation AC power source 30 in the exemplary embodiment according to FIG. 1, passive compensation members are provided in the embodiment according to FIG. 2. These passive compensation members comprise a ground connection, which extends at an output of the secondary winding of the isolation transformer 40 via a capacitor $C_K$ and a control transistor 16, as well as another ground connection, which extends via a resistor $R_K$ and a control transistor 18. The opposite output of the secondary winding of the isolation transformer 40 is connected to ground via a capacitor ½ $C_K$ and is likewise connected to ground via a resistor 2 $R_K$. The control and evaluating unit 20 acts on the control transistors of the passive compensation members via digital-analog converters 32 and 34 and controls the control transistors in order to thus shift the amplitude and the phase of the AC power source such that the common-mode signal, which is measured with the common-mode signal measuring electrode 4, is minimized.

The potential is set on the body against the ground via the center tap of the power source, either feeding here the compensation AC current according to value and phase to minimize the common-mode signal (FIG. 1) or establishing the measuring reference of the detected voltage signals of the other electrodes directly at the center tap of the isolation transformer 40, the compensation of the common-mode signal taking place by automatic passive detuning of the power source (FIG. 2).

It is also possible not to design the common-mode signal measuring electrode 4 as a separate electrode, but to use one of the measuring electrodes that is not being used on the circumference of the patient's body for the function thereof. The electrode selected for this, which is selected from among the electrodes that are not being used either for current feed or as the current measuring electrode pair right now, is connected via the multiplexer 60 to the measuring amplifier 62, and it can then be used in this manner in both the embodiment according to FIG. 1 and that according to FIG. 2. This has, furthermore, the advantage that the common-mode signal measuring electrode 4 can now always be located, as desired, in the vicinity of the current measuring electrodes, where the common-mode signal is to be eliminated for the most part.

The control and evaluating unit is set up in this exemplary embodiment to store the control parameters for detuning the symmetrical AC power source, which parameters are determined to minimize the common-mode signal, for each electrode pair, to poll the corresponding control parameters for detuning the symmetrical AC power source for each currently connected electrode pair in the measuring mode, and to detune the symmetrical AC power source according to these parameters individually for each currently connected electrode pair.

Figure 5:
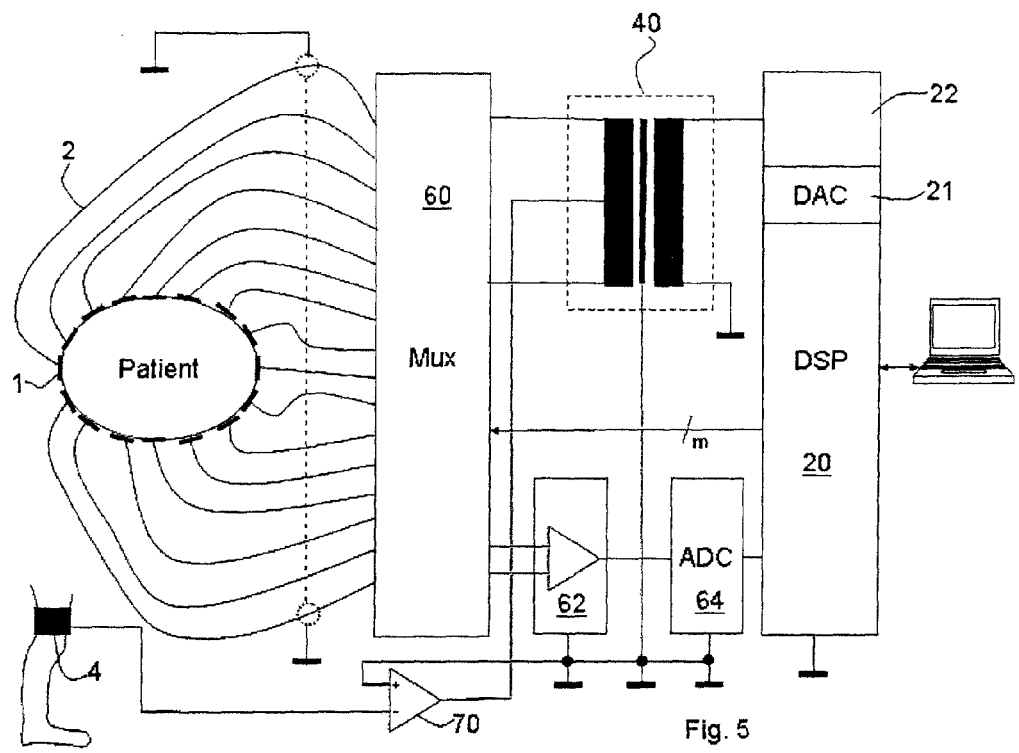
FIG. 5 shows an embodiment of an electroimpedance tomograph according to the present invention according to an alternative solution.

FIG. 5 shows an embodiment according to the alternative aspect of the present invention. Identical components are designated by the same reference numbers as in the preceding figures. Unlike in the preceding embodiments, the overall AC power unit includes an analog control loop circuit with a differential amplifier 70. This amplifier 70 receives as input signals at first the output signal of a common-mode signal measuring electrode 4, which supplies the common-mode signal on the body. The other input of the differential amplifier is connected to ground. The output of the differential amplifier 70 is fed into the center tap of the symmetrical AC power source 22. This power source 22 is detuned hereby until the common-mode signal on the body is minimized. The individual detuning of the AC power source is performed in this embodiment by the control circuit for each currently connected electrode pair repeatedly in the measuring mode.

Figure 4:
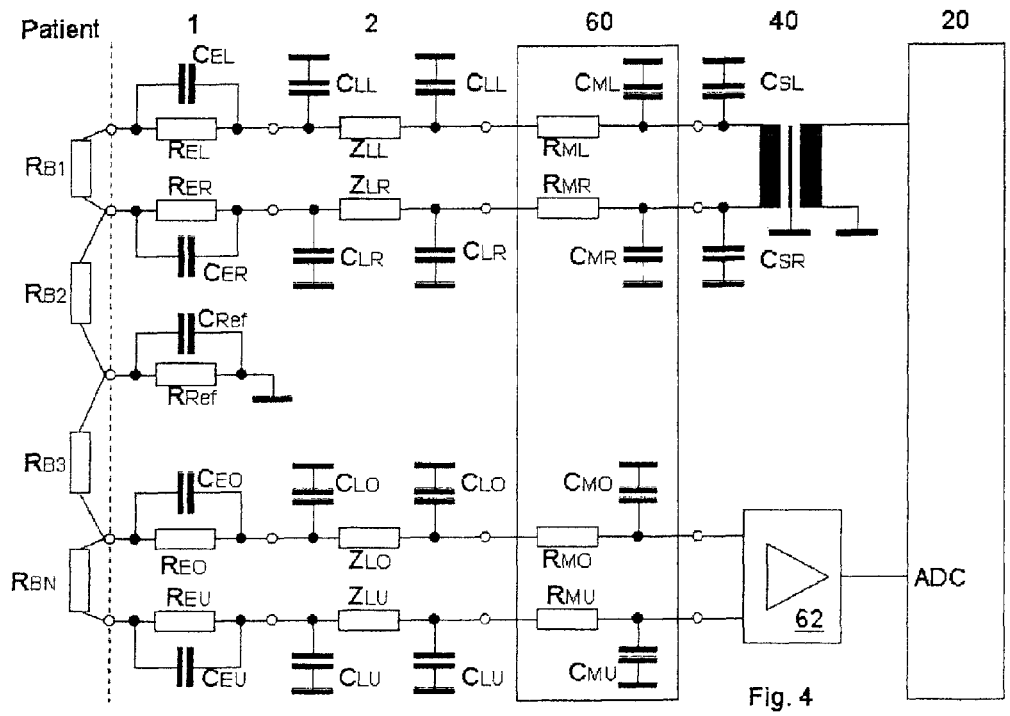
FIG. 4 is an equivalent circuit for explaining the asymmetry developing in the device according to FIG. 1.
Figure 6:
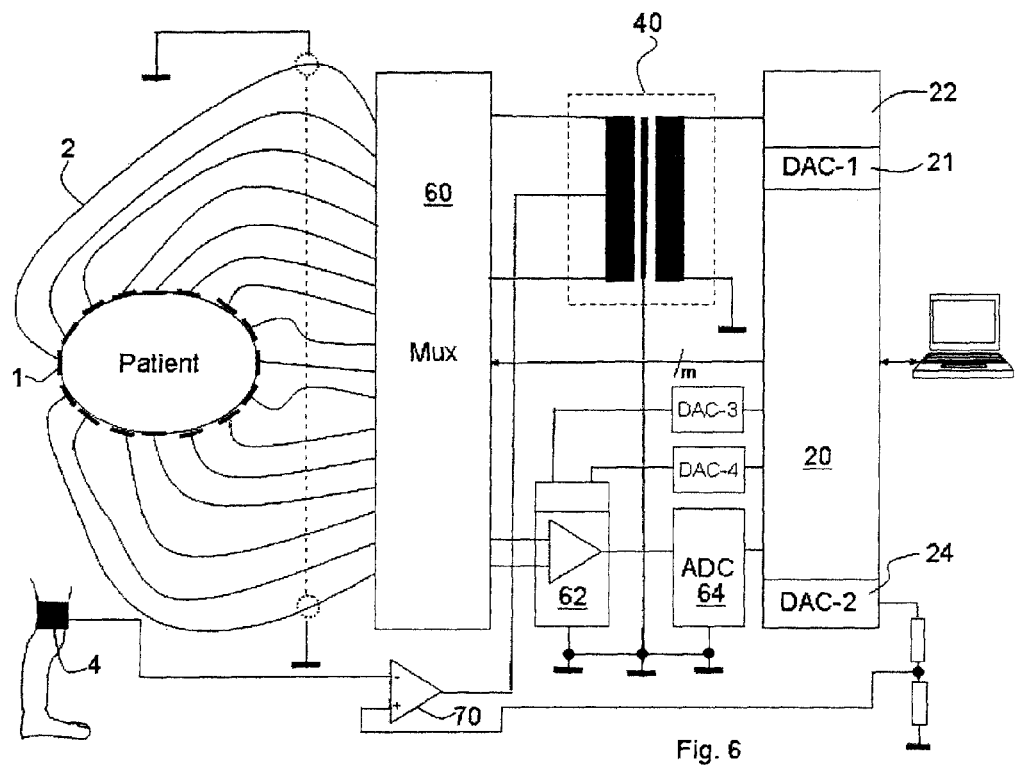
FIG. 6 is a variant of the embodiment according to FIG. 5.

FIG. 6 shows an embodiment of an electroimpedance tomograph, which has the adjusting function via an analog control circuit as in the embodiment according to FIG. 4. Moreover, the electroimpedance tomograph according to this embodiment is provided with additional components and program-technical setups of the control and evaluating unit 20, which make possible an expanded functionality. In the normal measuring mode, the control and evaluating unit 20 controls a digital-analog converter 24 such that its output is grounded. The second input of the differential amplifier 70 is consequently connected to the ground in this state, as in the exemplary embodiment according to FIG. 5, so that the analog control loop circuit with the differential amplifier 70 can compensatingly detune the symmetry of the AC power source 22 in a corresponding manner for each electrode pair in order to achieve optimal common-mode signal suppression.

Moreover, the control and evaluating unit 20 is set up to provide a common-mode signal at the voltage divider shown in an adjusting mode of operation before the measuring mode via the digital-analog converter 24. Since this additional common-mode signal is fed into the analog control circuit with the differential amplifier 70, a common-mode signal is correspondingly also generated on the patient's body by detuning the AC power source 22. The control and evaluating unit 20 is set up, furthermore, to adjust the measuring amplifier 62 according to value and phase during this adjusting phase for each electrode pair such that the common-mode signal at the output of the measuring amplifier 62 is minimized, and the adjusted parameters are stored for each electrode pair. This device is consequently able to purposefully apply an additional common-mode signal to the body via common-mode signal electrodes during an adjusting phase. This common-mode signal also propagates via the electrodes 1 and the selector switch 60 to the measuring amplifier 62. The control and evaluating unit 20 is set up, furthermore, to adjust the measuring amplifier 62, for which purpose digital-analog converters are connected to the control and evaluating unit 20 and to the measuring amplifier 62 in order to make it possible to adjust the measuring amplifier 62 according to value and phase. Consequently, the common-mode signal, which was applied purposefully and propagates into the measuring amplifier 62, is consequently minimized at the output of the measuring amplifier 62 during the adjusting phase for each electrode pair by setting the measuring amplifier 62. The adjusted parameters for the measuring amplifier 62, which are needed for this for each electrode pair, are kept ready in a stored form in the control and evaluating unit 20. The measuring amplifier 62 is then adjusted in the measuring mode proper for each connected electrode pair with the adjusted parameters determined before. Moreover, the analog control circuit with the differential amplifier 70 will then act to further suppress any common-mode components that may still be present.

While specific embodiments of the invention have been shown and described in detail to illustrate the application of the principles of the invention, it will be understood that the invention may be embodied otherwise without departing from such principles.

What is claimed is:

1. An electroimpedance tomography comprising:
a plurality of electrodes for placement on a body of a patient;
a control and evaluating unit;
a selector switch;
a measuring amplifier;
an AD converter;
a symmetrical AC power source used to reduce common-mode signals, said electrodes being connected to said control and evaluating unit via said selector switch, wherein said control and evaluating unit cooperates with said selector switch such that two of said electrodes as an electrode pair are each supplied with an alternating current from said symmetrical AC power source and the detected analog voltage signals of the other said electrodes are processed in order to reconstruct therefrom the impedance distribution of the body in the plane of the electrodes; and
a common-mode signal measuring electrode, said control and evaluating unit detuning the common-mode signal of the alternating current applied on the body with respect to an electrical ground by means of said common-mode signal measuring electrode and, based on this, the symmetry of said symmetrical AC power source such that the common-mode signal on the body is minimized, and the corresponding detuning parameters are stored for each electrode pair.

2. An electroimpedance tomography in accordance with claim 1, wherein said control and evaluating unit is set up in a measuring mode to poll the detuning parameters determined for minimizing the common-mode signal for a particular electrode pair being connected and to detune the symmetrical AC power source according to these parameters.

3. An electroimpedance tomography in accordance with claim 1, further comprising a compensation AC power source having an output that is sent to the symmetrical AC power source, and said control and evaluating unit is set up to control an amplitude and phase of said output of said compensation AC power source such as to detune the symmetry of said symmetrical AC power source in order to minimize the common-mode signal on the body.

4. An electroimpedance tomograph in accordance with claim 3, further comprising an isolation transformer inserted between said symmetrical AC power source and said selector switch, wherein an output of a secondary winding of said isolation transformer forms the output of said symmetrical AC power source.

5. An electroimpedance tomography in accordance with claim 4, wherein said compensation AC power source is connected to a center tap of said secondary winding of said isolation transformer.

6. An electroimpedance tomograph in accordance with claim 1, further comprising passive compensation members connected to a first output of said symmetrical AC power source, wherein said compensation members have at least one resistor, at least one capacitor, and at least one control transistor, and said control and evaluating unit is set up to control said compensation members via at least one control transistor such that the symmetry of said symmetrical AC power source is detuned such as to minimize the common-mode signal on the body.

7. An electroimpedance tomograph in accordance with claim 6, wherein another output of said symmetrical AC power source is detuned in advance by passive compensation members in the opposite sense so that an adjusting point can be reached according to value and phase of a signal at the first output with certainty by means of said compensation members and said at least one control transistor in order to minimize the common-mode signal on the body.

8. An electroimpedance tomograph in accordance with claim 6, wherein a first passive compensation member at the first output of said symmetrical AC power source is connected to ground via a resistor and a control transistor, and a second compensation member is connected to ground via a capacitor and a control transistor.

9. An electroimpedance tomograph in accordance with claim 7, wherein a first passive compensation member, which has a resistor connected to ground, is connected to the other output of said symmetrical AC power source, and a second compensation member, which has a capacitor, which is connected to the ground, is connected, so that said symmetrical AC power source is detuned from the very beginning in the opposite sense in relation to said compensation members at the first output, so that an adjusting point can be reached with certainty according to value and phase of the signal at the first output by means of said compensation members and said control transistors in order to minimize the common-mode signal on the body.

10. An electroimpedance tomograph comprising:
a plurality of electrodes, which can be placed on a body of a patient;
a control and evaluating unit connected to said plurality of electrodes;
a symmetrical AC power source used to reduce common-mode signals;
a selector switch, said control and evaluating unit cooperating with said selector switch such that each of two electrodes forming an electrode pair are supplied with an alternating current from said symmetrical AC power source and the detected analog voltage signals of the other electrodes are processed in order to reconstruct therefrom the impedance distribution of the body in the plane of the electrodes;
a common-mode signal measuring electrode;
an analog control loop circuit with a differential amplifier, where one input of said differential amplifier is connected to ground and the other input thereof is connected to an output of said common-mode signal measuring electrode, said analog control loop circuit supplying a common-mode signal of the alternating current on the body, and that the output of said differential amplifier is connected to a center tap of said symmetrical AC power source in order to detune said symmetrical AC power source such that the common-mode signal on the body is minimized.

11. An electroimpedance tomograph in accordance with claim 10, wherein:
a measuring amplifier receives the detected analog voltage signals from said selector switch;
said control and evaluating unit is set up to provide, at one output, during an adjusting mode of operation, an additional common-mode signal, which is connected to ground outside the adjusting mode of operation, wherein one input of said differential amplifier is connected to this output, and that said control and evaluating unit is setup, furthermore, to adjust a signal from said measuring amplifier according to value and phase during the adjusting mode of operation for each electrode pair connected by said selector switch such that the common-mode signal at the output of said measuring amplifier is minimized, and parameters for adjusting said measuring amplifier are stored for each electrode pair.

12. An electroimpedance tomograph in accordance with claim 11, wherein said control and evaluating unit is set up to poll the corresponding adjusted parameters in the measuring mode for each connected electrode pair and to adjust the signal from said measuring amplifier according to these adjusted parameters according to value and phase.

13. An electroimpedance tomograph in accordance with claim 11, wherein said control and evaluating unit is set up to provide the additional common-mode signal in an adjusting mode of operation with the same frequency as that of said symmetrical AC power source.

14. An electroimpedance tomograph in accordance with claim 13, wherein:
a measuring amplifier receives the detected analog voltage signals from said selector switch;
said control and evaluating unit provides, at one output, during an adjusting mode of operation, an additional common-mode signal, which is connected to ground outside the adjusting mode of operation, wherein one input of said differential amplifier is connected to this output, and that said control and evaluating unit adjusts a signal from said measuring amplifier according to an amplitude and phase during the adjusting mode of operation for each electrode pair connected by said selector switch such that the common-mode signal at the output of said measuring amplifier is minimized, and parameters for adjusting said measuring amplifier are stored for each electrode pair.

15. An electroimpedance tomography in accordance with claim 1, wherein:
said symmetrical AC power source is connected to one of;
i) a compensation AC power source having an output that is sent to the symmetrical AC power source, and said control and evaluating unit is arranged to control an amplitude and phase of said output of said compensation AC power source according to amplitude and phase such as to detune the symmetry of said symmetrical AC power source in order to minimize the common-mode signal on the body; or;
ii) passive compensation members connected to a first output of said symmetrical AC power source, wherein said compensation members have at least one resistor, at least one capacitor, and at least one control transistor, and said control and evaluating unit is arranged to control said compensation members via said at least one control transistor such that the symmetry of said symmetrical AC power source is detuned such as to minimize the common-mode signal on the body;

said control and evaluating unit is set up in a measuring mode to poll detuning parameters determined for minimizing the common-mode signal for a particular electrode pair being connected and to detune the symmetrical AC power source according to these parameters.

16. An electroimpedance tomography comprising:
a plurality of electrodes for placement on a body;
a selector switch connected to said plurality of electrodes;
an AC power unit connected to said selector switch and generating an applied alternating current;
a measuring amplifier connected to said selector switch;
a control and evaluating unit controlling said selector switch to selectively supply two of said electrodes with the applied alternating current from said AC power unit, said control and evaluating unit also controlling said selector switch to selectively send detected analog voltage signals of the other said electrodes to said control and evaluating unit to reconstruct from said detected analog voltage signals an impedance distribution of the body in a plane of said plurality of electrodes;
a common-mode signal measuring electrode connected to the body and to said AC power unit, said common-mode signal measuring electrode generating a common-mode signal of a body current on the body with respect to an electrical ground, said AC power unit receiving the common-mode signal and modifying the applied alternating current based on the common mode signal to minimize the common-mode signal of the body current.

17. An electroimpedance tomography in accordance with claim 16, wherein:
said AC power unit includes a symmetrical AC power source, and portions of said control and evaluating unit to control and modify said symmetrical AC power source based on said common-mode signal.

18. An electroimpedance tomography in accordance with claim 16, wherein:
said AC power unit includes a symmetrical AC power source with a center tap transformer and with an analog control loop circuit, said common-mode signal measuring electrode being connected to said analog control loop circuit, which is then connected to a center tap of said center tap transformer to modify the applied alternating current from said AC power unit to minimize the common-mode signal of the body current.

19. An electroimpedance tomography in accordance with claim 16, wherein:
said control and evaluating unit operates in a measuring mode to determine AC power unit parameters that minimizing the common-mode signal for each pair of said plurality of electrodes, said control and evaluating unit modifies said AC power unit according to said AC power unit parameters when a respective said each pair of said plurality of electrodes is used to applied the applied alternating current to the body.

20. An electroimpedance tomography in accordance with claim 17, wherein:
said AC power unit includes a compensation AC power source with an output in connection with an output of said symmetrical AC power source, said control and evaluating unit controlling an amplitude and phase of said output of said compensation AC power source in order to modify the applied alternating current from said symmetrical AC power source in order to minimize the common-mode signal on the body.

21. An electroimpedance tomograph in accordance with claim 17, wherein:
said AC power unit includes passive compensation members connected to a first output of said symmetrical AC power source, said compensation members having a resistor, a capacitor, and a control transistor, said control and evaluating unit controlling said compensation members via said control transistor such that a symmetry of said symmetrical AC power source is modified to minimize the common-mode signal on the body.

* * * * *